(12) United States Patent
Zeng et al.

(10) Patent No.: US 12,180,183 B2
(45) Date of Patent: Dec. 31, 2024

(54) WATER-SOLUBLE FLUORESCENT PROBE AND NANOPARTICALS WITH AGGREGATION-INDUCED EMISSION EFFECT FOR OVARIAN CANCER AND PREPARATION METHOD AND USE THEREOF

(71) Applicant: HUNAN TARGETING DETECTION TECHNOLOGY CO., LTD, Hunan (CN)

(72) Inventors: Wenbin Zeng, Changsha (CN); Shi Li, Changsha (CN); Zuyuan Liu, Changsha (CN); Xueyan Huang, Changsha (CN); Tang Gao, Changsha (CN)

(73) Assignee: HUNAN TARGETING DETECTION TECHNOLOGY CO., LTD., Hunan (CN)

( * ) Notice: Subject to any disclaimer, the term of this patent is extended or adjusted under 35 U.S.C. 154(b) by 1033 days.

(21) Appl. No.: 17/257,884

(22) PCT Filed: Jun. 24, 2019

(86) PCT No.: PCT/CN2019/092455
§ 371 (c)(1),
(2) Date: Jan. 5, 2021

(87) PCT Pub. No.: WO2020/007210
PCT Pub. Date: Jan. 9, 2020

(65) Prior Publication Data
US 2021/0269421 A1    Sep. 2, 2021

(30) Foreign Application Priority Data
Jul. 5, 2018 (CN) .......................... 201810727137.5

(51) Int. Cl.
C07D 401/00 (2006.01)
C07D 401/14 (2006.01)
(Continued)

(52) U.S. Cl.
CPC ............ C07D 401/14 (2013.01); C09K 11/06 (2013.01); G01N 21/6428 (2013.01);
(Continued)

(58) Field of Classification Search
CPC .................................................. C07D 401/14
(Continued)

(56) References Cited

FOREIGN PATENT DOCUMENTS

| CN | 106518965 A | 3/2017 |
| CN | 106632305 A | 5/2017 |
| CN | 106699734 A | 5/2017 |

OTHER PUBLICATIONS

Gao et al. "Smart Self-Assembled Organic Nanoprobe for Protein-Specific Detection: Design, Synthesis, Application, and Mechanism Studies" Anal. Chem. 2017, 89, 10085-10093 Plus Supporting Information (Year: 2017).*

(Continued)

*Primary Examiner* — Christine T Mui
*Assistant Examiner* — Emily R. Berkeley
(74) *Attorney, Agent, or Firm* — Cooper Legal Group, LLC

(57) ABSTRACT

Disclosed are a water-soluble fluorescent probe and nanoparticles with an aggregation induced emission (AIE) effect and preparation methods and the application. The fluorescent probe molecule includes one imidazole ring substituted by two methoxyphenyls and one phenyl and two quaternary ammonium salt structures. It has good dispersion in water, may form micelles. It has the characteristics of AIE effect and a large Stokes shift etc. It is suitable for fluorescence detection. Under the induction of lysophosphatidic acid, the (Continued)

probe can be self-assembled so as to aggregate and generate yellow fluorescence. Lysophosphatidic acid may be quantitatively analyzed by measuring the intensity of emitted fluorescence.

7 Claims, 5 Drawing Sheets

(51) Int. Cl.
*C09K 11/06* (2006.01)
*G01N 21/64* (2006.01)
*G01N 33/574* (2006.01)
*G01N 33/58* (2006.01)
*G01N 33/92* (2006.01)

(52) U.S. Cl.
CPC ..... *G01N 33/57449* (2013.01); *G01N 33/582* (2013.01); *G01N 33/92* (2013.01); *C09K 2211/1018* (2013.01)

(58) Field of Classification Search
USPC .......................................................... 436/64
See application file for complete search history.

(56) References Cited

OTHER PUBLICATIONS

Tjutrins et al. "A palladium-catalyzed synthesis of (hetero)arylsubstituted imidazoles from aryl halides, imines and carbon monoxide" Chem. Sci., 2017, 8, 1002-1007 (Year: 2017).*
International Search Report in the international application No. PCT/CN2019/092455, mailed on Sep. 30, 2019, 3 pgs.
English translation of the Written Opinion of the International Search Authority in the international application No. PCT/CN2019/092455, mailed on Sep. 29, 2019, 5 pgs.
"A Self-Assembled Nanoprobe for Long-Term Cancer Cell Nucleus-Specific Staining and Two-Photon Breast Cancer Imaging"; Feb. 2018; Tang Gao, Shuanglian Wang, Wuwulv Lv, Mian Liu, Hongliang Zenh, Zhu Chen, Jie Dong, Ziping Wu, Xueping Feng and Wenbin Zeng; Chemical Communications (Cambridge, United Kingdom), vol. 29, No. (54), pp. 3578-3581, 14 pgs.
"Smart Self-Assembled Organic Nanoprobe for Protein-Specific Detection: Design, Synthesis, Application, and Mechanism Studies"; Aug. 2017; Tang Gao, Shuqi Yang, Xiaozheng Cao, Jie Dong, Ning Zhao, Peng Ge, Wenbin Zeng and Zhen Cheng; Analytical Chemistry (Washington, DC, United States), vol. 18, No. (89), 29 pgs.
"Dibenzo[a,c]phenazine-derived near-infrared fluorescence biosensor for detection of lysophosphatidic acid based on the aggregation-induced emission", Nov. 2015, Tao Jiang, Niannian Lu, Ji Yang, Yandi Hang, Jian Wang, Ping Zhao and Jianli Hua, RSC Advances, Issue 124, vol. 5, reprinted from the Internet at: https://pubs.rsc.org/en/content/articlelanding/2015/ra/c5ra21408d, 6 pgs.
"Lysophospholipid Growth Factors in the Initiation, Progression, Metastases, and Management of Ovarian Cancer", Apr. 2000, Xianjun Fang, Douglas Gaudette, Tatsuro Furui, Muling Mao, Veronica Estrella, Astrid Eder, Terri Pustilnik, Takayo Sasagawa, Ruthie Lapushin, Shiangxing Yu, Robert B. Jaffe, Jon R. Wiener, James R. Erickson and Gordon B. Mills, Annals New York Academy of Science, Reprinted from the Internet at: https://pubmed.ncbi.nlm.nih.gov/10818454/n, pp. 188-208.
"Lysophosphatidic Acid as a Potential Biomarker for Ovarian and Other Gynecologic Cancers", Aug. 1998, Yan Xu, Zhongzhou Shen, Donald Wiper, Minzhi Wu, Richard Morton, Paul Eison, Alexander Kennedy, Jerome Belinson and Maurie Markman, Jama, vol. 280, No. 8, Reprinted from the Internet at: https://pubmed.ncbi.nlm.nih.gov/9728644/, pp. 719-723.
"Iran: Promises and Prospects for Health", Mar. 2016, The Lancet, vol. 387, Issue 10022, Reprinted from the Internet at: https://www.thelancet.com/journals/lancet/article/PIIS0140-6736(16)00630-9/fulltext, p. 918.
"Evaluation of Plasma Lysophospholipids for Diagnostic Significance Using Electrospray Ionization Mass Spectrometry (ESI-MS) Analyses", Apr. 2006, Yijin Xiao, Yonghong Chen, Alexander W. Kennedy and Jerome Belinson, Annals of the New York Academy of Sciences, Reprinted from the Internet at: https://pubmed.ncbi.nlm.nih.gov/10818458/, pp. 242-259.
"Quantitative Analysis of Lysophosphatidic Acid by Time-of-Flight Mass Spectrometry using a Phosphate-Capture Molecule", Jun. 2004, Tamotsu Tanaka, Hideki Tsutsui, Kaoru Hirano, Tohru Koike, Akira Tokumura and Kuyoshi Satouch, Journal of Lipid Research, vol. 45,, Reprinted from the Internet at: https://pubmed.ncbi.nlm.nih.gov/15314093/. pp. 2145-2150.
"Copolythiophene-Derived Colorimetric and Fluorometric Sensor for Lysophosphatidic Acid Based on Multipoint Interactions", Mar. 2013, Minhuan Lan, Weimin Liu, Ying Wang, Jiechao Ge, Jiasheng, Wu, Hongyan Zhang, Jianhong Chen, Wenjun Zhang and Pengfei Wang, ACS Applied Materials & Interfaces, 5(6), reprinted from the Internet at: https://pubs.acs.org/doi/10.1021/am400319g, pp. 2283-2288.

* cited by examiner

WATER-SOLUBLE FLUORESCENT PROBE AND NANOPARTICALS WITH AGGREGATION-INDUCED EMISSION EFFECT FOR OVARIAN CANCER AND PREPARATION METHOD AND USE THEREOF

TECHNICAL FIELD

The present invention relates to a fluorescent probe and nanoparticles, and in particular to a water-soluble fluorescent molecular probe or fluorescent nanoparticles with an aggregation-induced emission (AIE) effect, and a preparation method thereof, in particular further to use of the fluorescent molecular probe and nanoparticles in detection of lysophosphatidic acid. The disclosure belongs to the technical field of chemical analysis and bioanalysis detection.

BACKGROUND ART

Lysophosphatidic acid (LPA) is the smallest and simplest glycerophospholipids found so far, and consists of a hydrophilic terminal containing a phosphoric acid and a hydrophobic terminal containing a long fatty chain. It is a normal ingredient of serum and is generated by platelets during platelet aggregation. As a cell membrane lipid derivative and metabolic intermediate, LPA mediates a wide range of biochemical, physiological and pathological processes, such as stimulating cell proliferation, differentiation and migration, smooth muscle contraction, neurotransmitter release and promoting platelet aggregation. Recent studies show that ovarian cancer cells would produce LPA which could act as an activating factor for ovarian cancer. The normal physiological concentration of LPA in plasma is about 0.1 μM-6.3 μM, while a plasma LPA level is significantly elevated in a patient with ovarian cancer. Therefore, to quantitatively evaluate the plasma LPA level may be used as a potential biomarker for detecting human ovarian cancer. A critical value of LPA is 1.3 μM, and the sensitivity and specificity thereof for diagnosis of the patient with ovarian cancer are as high as 95% and 92%, respectively. (X. Fang, D. Gaudette, T. Furui, M. Mao, V. Estrella, A. Eder, T. Pustilnik, T. Sasagawa, R. Lapushin, S. Yu, R. B. Jaffe, J. R. Wiener, J. R. Erickson and G. B. Mills, Ann. N. Y. Acad. Sci., 2000, 905, 188; Y. Xu, Z. Shen, D. W. Wiper, M. Wu, R. E. Morton, P. Elson, A. W. Kennedy, J. Belinson, M. Markman and G. Casey, J. Am. Med. Assoc. 1998, 280, 719). Ovarian cancer is a highly metastatic disease characterized by widespread peritoneum and ascites. It is a main cause of death from gynecological malignancies and poses a serious threat to women lives. Because early symptoms of ovarian cancer are not apparent, about 60% of patients with ovarian cancer are diagnosed at a late stage of the disease, which affects the treatment effect. Therefore, if ovarian cancer may be detected earlier by screening and treated more promptly, it may gain the upper hand against this stubborn disease. Effective early diagnosis of ovarian cancer is essential to improve overall survival (Anonymous, Lancet, 2016, 387, 918.). It may be seen that developing a simple, specific and effective method for LPA detection is urgent and important for prevention and diagnosis of ovarian cancer.

So far, some methods for detecting the plasma LPA level have been developed. Typical methods include electrospray ionization mass spectrometry (ESI-MS), matrix-assisted laser desorption ionization mass spectrometry (MALDI-MS), GC-MS and the others. Although such technologies show high sensitivity, they usually require laborious sample pretreatment, sample derivatization or longtime separation, and require expensive devices to complete the analysis. Thus, they are not suitable for routine diagnosis (Y. J. Xiao, Y. H. Chen, W. K. Alexander, B. Jerome and Y. Xu, Ann. Ny. Acad. Sc, 2000, 905, 242; T. Tanaka, H. Tsutsui, K. Hirano, T. Koike, A. Tokumura and K. Satouchi, J. Lipd. Res., 2004, 45, 2145.). In recent years, some new methods of quantitative analysis of LPA have also been developed, such as a capillary electrophoresis indirect ultraviolet detection method, and enzyme-linked immunoassay (ELISA). Although these methods are specific and the instruments are relatively simple, the operation is quite complicated. ELISA kits for LPA detection on the market are stringent in operation conditions because enzyme reagents used thereof are easily affected by the environment and some substrates are volatile or sensitive to light. Moreover, some operation steps not only require incubation for 30 minutes or 1 hour, but also are relatively cumbersome, and have certain limitation. On the other hand, the fluorescent probes attract widespread attention due to its characteristics of high sensitivity, simplicity and convenience, and real-time analysis. However, the probes examples for detecting LPA are rare. Wu Junchen et al. reported a polypeptide probe which may specifically recognize LPA. It may specifically bind to LPA in vivo and concentrate on tumor sites. It shows the potential to recognize LPA in serum and emit enhanced fluorescence in vitro. However, the good linear relationship for the detection LPA concentration is in the range of 6-20 μM. If used as a real-time and rapid detection method to detect LPA for clinical diagnosis of ovarian cancer, an accurate detection result may not be obtained since the LPA concentration exceeds this range (Wu Junchen, Polypeptide Probe for Specifically Recognizing Lysophosphatidic Acids and Preparation and Use thereof, China, 106518965 A[P] 0.2017.03.22.). Lan Minhuan et al. designed a fluorescent probe, 3-phenylthiophene-based water-soluble copolythiophene (CPT9), for the fluorometric detection of LPA. The probe could specifically recognize LPA based on electrostatic interaction, hydrophobic interaction and hydrogen bonding, which was designed by taking advantage of the characteristics of LPA with rich negative charge and a long hydrophobic chain. Although it has high sensitivity and high selectivity, this probe is a conjugated polymer synthesized with many synthesis steps. Compared with small molecule fluorescent probes, its background noise may be higher. (M. H. Lan, W. M. Liu, Y. Wang, J. C. Ge, J. C. Wu, H. Y. Zhang, J. H. Chen, W. J. Zhang and P. F. Wang, ACS Appl. Mater. Interfaces, 2013, 5, 2283.). In addition, these few fluorescent probes which may be used to detect LPA tend to form aggregates in buffers and result in the aggregation-caused quenching (ACQ), and thus cause temporal and spatial instability. Therefore, it is important to design a water-soluble fluorescent probe which can quantitatively analyze LPA in real-time with high sensitivity and selectivity and can overcome the defect of aggregation-caused quenching.

SUMMARY

In order to overcome the disadvantages of existing fluorescent probes for detecting lysophosphatidic acid (LPA), a first aim of the disclosure is to provide a fluorescent molecular probe with good water solubility and an aggregation-induced emission effect (AIE), which is used for specifically recognizing a marker of ovarian cancer, namely LPA.

A second aim of the disclosure is to provide a fluorescent molecular probe for specifically recognizing LPA, which has the aggregation-induced emission effect and may be self-assembled to form nanoparticles in an aqueous solution.

A third aim of the disclosure is to provide a method for preparing the fluorescent molecular probe, in which raw materials are easily available and operations are simple.

A fourth aim of the disclosure is to provide a method for preparing the fluorescent probe and nanoparticles, in which operations are simple and conditions are mild.

A fifth aim of the disclosure is to provide use of the fluorescent probe for detecting LPA in blood and other samples. The fluorescent molecular probe is self-assembled in the aqueous solution to form nanoparticles with large sizes and loose structures. Through electrostatic interaction and hydrophobic force between LPA and the fluorescent molecular probes, the fluorescent probes are aggregated. Once aggregated, the rotation of probe is restricted and the fluorescence is emitted. Therefore, the detection of LPA is highly sensitive, selective and stable.

In order to achieve the above technical aims, the disclosure provides a water-soluble fluorescent molecular probe for specifically recognizing LPA. The water-soluble fluorescent molecular probe has the aggregation-induced emission effect, and has a structure of Formula 1.

Formula 1

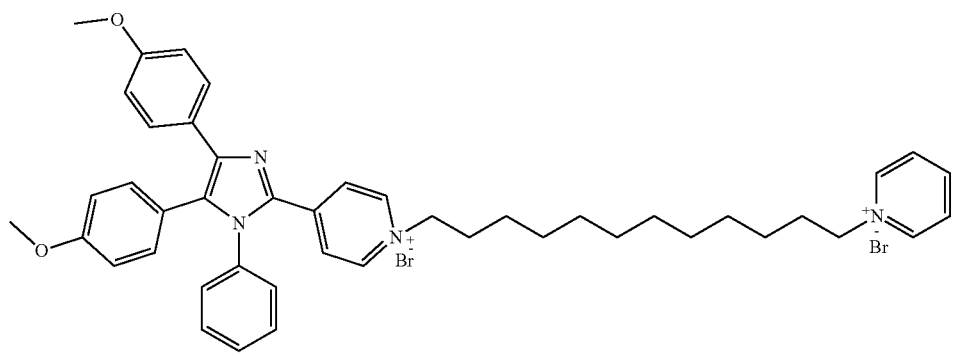

The fluorescent molecular probe for specifically recognizing LPA according to the disclosure has the characteristics of the aggregation-induced emission effect (AIE). The fluorescent molecular probe emits strong fluorescence at 500-600 nm under excitation of 400 nm, and has a large Stokes shift.

The disclosure further provides fluorescent probe and nanoparticles for specifically recognizing LPA, which is formed by self-assembly of the fluorescent molecular probes.

The disclosure further provides a method for preparing the water-soluble fluorescent molecular probe with the aggregation-induced emission effect for specifically recognizing LPA. The method includes the following steps.

1) 4-formylpyridine, aniline and anisil undergo a one-pot cyclization reaction in an acetic acid/ammonium acetate system, to obtain an intermediate of Formula 2.
2) The intermediate of Formula 2 and 1,12-dibromododecane undergo a nucleophilic substitution reaction, to obtain an intermediate of Formula 3.
3) The intermediate of Formula 3 and pyridine undergo a nucleophilic substitution reaction, to yield the target product.

Formula 2

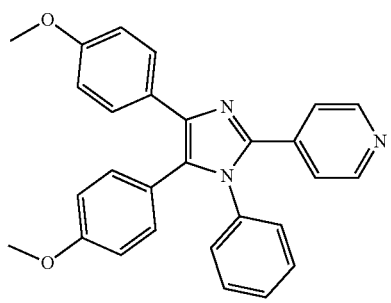

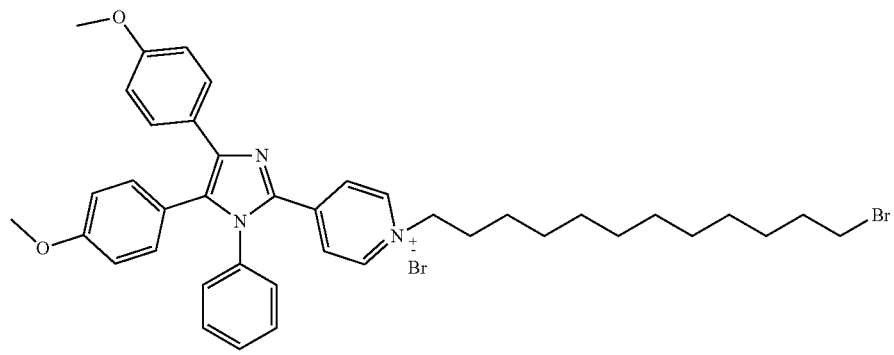

Formula 3

A specific preparation process is described as follows.

A reaction process in the step 1) is as follows: 4-formylpyridine and anilines are dissolved in a glacial acetic acid solvent and stirred for 0.5-1.5 hours at room temperature, and then anisil and ammonium acetate are added, and the reaction lasts for 6-12 hours at 120° C.

Reaction conditions in the step 2) are as follows: acetonitrile is used as a solvent, and the reaction lasts for 6-10 hours at 90° C.

Reaction conditions in the step 3) are as follows: pyridine is used as a solvent, and the reaction lasts for 6-10 hours at 90° C.

The disclosure further provides a method for preparing the organic fluorescent molecular probe and nanoparticles for specifically recognizing lysophosphatidic acid. After the fluorescent molecular probe is dissolved in an organic solvent, the obtained mixture is added into an aqueous solution, and then ultrasonic treatment is performed, to obtain the fluorescent molecular probe and nanoparticles.

In a preferred embodiment, the organic solvents are selected from at least one of methanol, ethanol, dimethylformamide, tetrahydrofuran, dimethyl sulfoxide, acetone, or acetonitrile.

The aqueous solutions are selected from pure water, physiological saline, a phosphate buffer solution (PBS), a tris(hydroxymethyl)aminomethane hydrochloride buffer solution or a 4-hydroxyethylpiperazine ethanesulfonic acid buffer solution.

The disclosure further provides the use of the fluorescent nanoprobe for specifically recognizing lysophosphatidic acid, in which detection of LPA is applied for diagnosing ovarian cancer.

In a preferred embodiment, the organic fluorescent nanoprobe is used for fluorescent quantitative analysis detection of LPA in a chemical solution system or blood of a subject.

The fluorescent probe of the disclosure has a tetrasubstituted imidazole ring and quaternary ammonium salt structures, which are linked by a long hydrophobic fatty chain in the middle. The fluorescent probe molecules have good water solubility, and can self-assemble in the aqueous solution to form nanoparticles with loose structures and without emitting fluorescence. After recognizing LPA, because LPA has high negative charge and a long hydrophobic fatty chain, the fluorescent probes are induced to be aggregated through intermolecular electrostatic interaction and hydrophobic force so that the rotation of the fluorescent molecules is restricted to generate strong yellow fluorescence. The detection mechanism thereof is shown in FIG. 5.

A preparation route of the water-soluble fluorescent molecular probe with the aggregation-induced emission effect for specifically recognizing LPA of the disclosure is as follows.

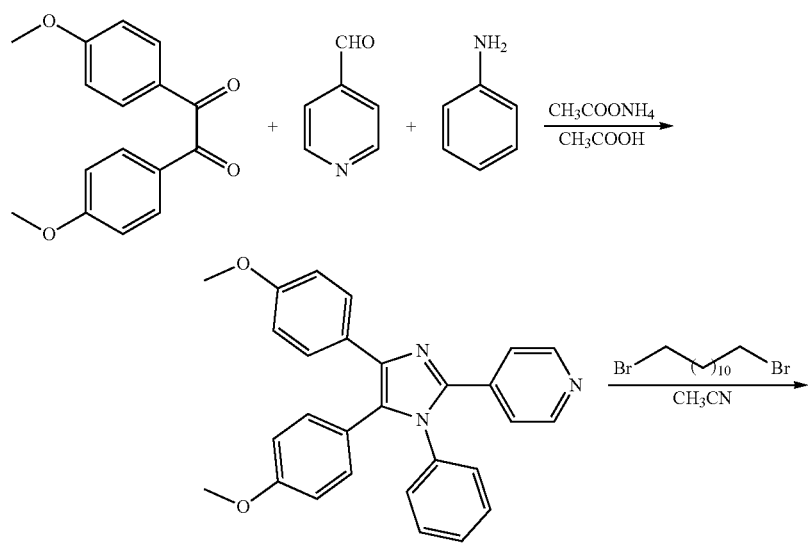

-continued

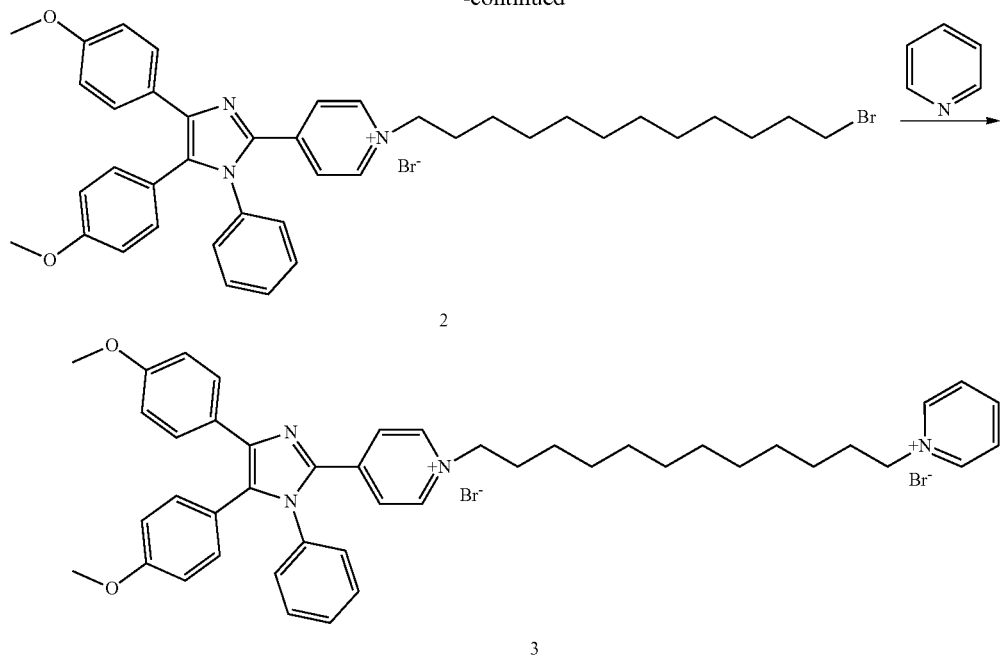

The specific preparation method for the water-soluble fluorescent molecular probe with the aggregation-induced emission effect for specifically recognizing LPA of the disclosure comprises the following steps.
  a. Aniline and 4-formylpyridine are dissolved in glacial acetic acid, and reacted for 1 hour under stirring at room temperature. After that, anisil and ammonium acetate are added to the mixture in sequence and are mixed uniformly. The reaction mixture is heated to 120° C. and refluxed overnight. After the reaction is completed by detecting with TLC, the reaction is quenched with water. The pH of the resulted mixture is adjusted to near neutral with a sodium hydroxide solution, and generation of a precipitation is observed, filtered and concentrated under vacuum to obtain a filter cake. The filter cake is dried. Compound 1 is obtained by purifying with the column chromatography.
  b. The compound 1 is dissolved in acetonitrile, into which 1,12-dibromododecane is added, and the obtained reaction system is mixed uniformly, and heated to reflux at 90° C. After the reaction is completed, the solvent is removed by distilling under vacuum. Compound 2 is obtained by purifying with column chromatography.
  c. The compound 2 is dissolved in pyridine. The obtained system is heated to 90° C. After the reaction is completed, the solvents are removed by distilling under vacuum. The target compound is obtained by purifying with the column chromatography.

The preparation method for the fluorescent molecular probe and nanoparticles for specifically recognizing LPA of the disclosure comprises the following steps.

The target compound is fully dissolved in an organic solvent to prepare a stock solution, and then the stock solution is sucked by a pipette and added to a certain amount of the aqueous solution under an ultrasonic condition. After the system is stirred for 30 min at room temperature, the organic nanoparticles for detecting LPA are obtained. The particle size and morphology of the formed nanoparticles are observed by dynamic light scattering (DLS) and scanning electron microscope (SEM).

A technical solution of the disclosure is proposed on the basis that the fluorescent molecular probes are self-assembled in the aqueous solution to form the nanoparticles with loose structures and the nanoparticle solution formed thereby has no fluorescence, and when lysophosphatidic acid is present, through the electrostatic interaction and hydrophobic force between the nanoparticle and lysophosphatidic acid, the fluorescent probes are aggregated to form an aggregation state so that rotation of the probe molecules is restricted to emit fluorescence. In this way, the fluorescent molecular probe and nanoparticles may be used for detecting lysophosphatidic acid. The disclosure establishes a method for detecting lysophosphatidic acid based on the above. The method has high selectivity and sensitivity, and may be widely popularized and applied.

The fluorescent molecular probe and nanoparticles of the disclosure may be used for detecting lysophosphatidic acid in a chemical simulation biological system and it may also be used for detecting lysophosphatidic acid in blood in clinical medicine.

Compared with the related art, the beneficial effects of the disclosure are as follows.
  1) The fluorescent molecular probe and nanoparticles for specifically recognizing lysophosphatidic acid of the disclosure have good water solubility, and they may be self-assembled to form non-fluorescent nanoparticles, and have the aggregation-induced emission effect. When the fluorescent molecular probe and nanoparticles are reacted with lysophosphatidic acid, an aggregation state may be formed, with an emission of fluorescence at 557 nm, which is especially suitable for the fluorescence detection.
  2) The preparation methods of the fluorescent molecular probe and nanoparticles for specifically recognizing lysophosphatidic acid of the disclosure are simple, low cost, and beneficial to the large-scale production.
3) The fluorescent molecular probe and nanoparticles of the disclosure may be used for detecting lysophosphatidic acid in blood and other samples. The probe has high selectivity to lysophosphatidic acid. The detection of lysophosphatidic acid is not interfered by serum albumin, proline, glycerin, phosphatidic acid, lysophosphatidyl choline and the others. The fluorescence intensity of the nanoparticle probe has a good linear relationship for the concentration of lysophosphatidic acid within a certain range from 0 to 33 μM, which indicates the characteristics of quantitative detection and can meet the clinical requirements for detecting the content of lysophosphatidic acid in blood.
4) The fluorescent molecular probe and nanoparticles of the disclosure has the advantages of fast response to lysophosphatidic acid, high sensitivity, high selectivity, and good stability. The detection is simple and efficient in operation, and low-cost, so that it is suitable for wide popularization and application.

DETAILED DESCRIPTION

Figure 1:
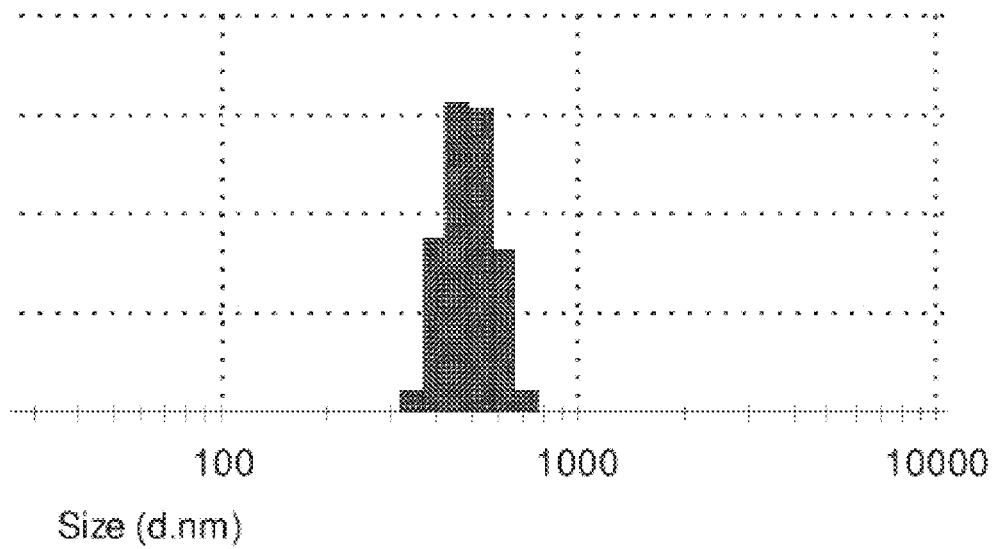
FIG. 1 is a dynamic light scattering diagram of the fluorescent molecular probe and nanoparticles prepared according to the disclosure.

The following Examples are intended to further illustrate the disclosure.

Example 1

Compound 3 with enhanced aggregation-induced fluorescence emission of the disclosure was synthesized with the followed synthetic route.

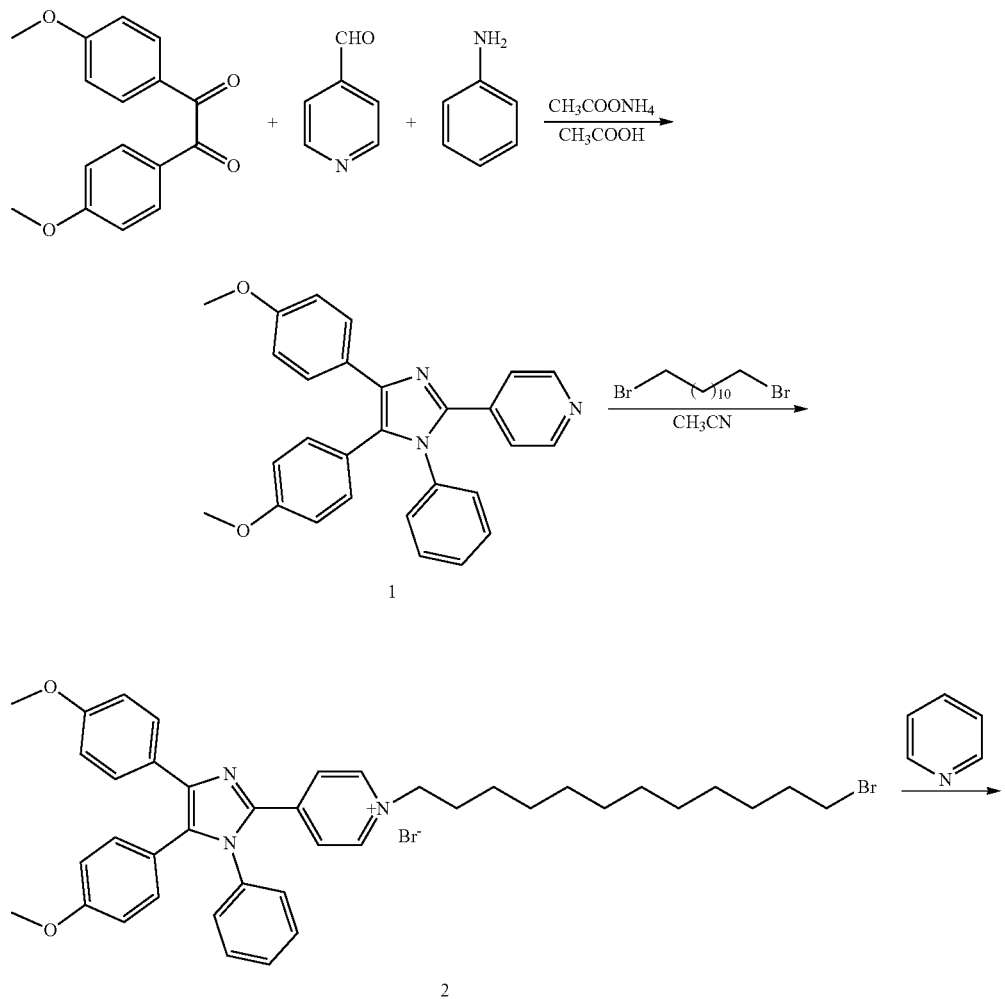

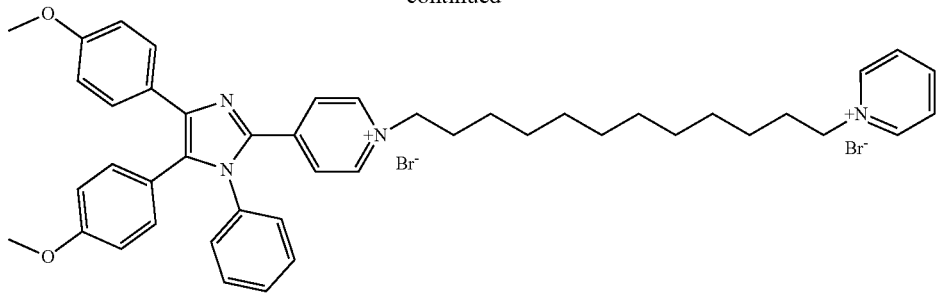

3

Synthesis of Compound 1

Aniline (93.1 mg, 1 mmol) and 4-formylpyridine (107.1 mg, 1 mmol) were weighed respectively and dissolved in 6-8 mL of glacial acetic acid. The obtained mixture was stirred for 1 hour at room temperature. Anisil (207.2 mg, 1 mmol) and ammonium acetate (462.5 mg, 6 mmol) were added in sequence into the reaction system. The reaction lasted overnight at 120° C., and the reaction was quenched with water. The reaction system was poured into 200 mL of iced water. A pH of the system was adjusted to neutral by using 0.1 mmol/L of sodium hydroxide solution. The mixture was filtered and washed with water for three times. After being dried under vacuum, a product was obtained by purifying with the silica gel column chromatography in a yield of 21.9%. Results of nuclear magnetic resonance analysis were as follows: $^1$H NMR (500 MHz, CDCl$_3$) δ 8.47 (d, 2H), 7.55 (d, 2H), 7.45-7.25 (m, 5H), 7.09 (t, 2H), 7.05 (d, 2H), 6.83 (d, 2H), 6.78 (d, 2H), 3.79 (d, 6H). $^{13}$C NMR (100 MHz, CDCl$_3$) δ 159.40, 158.64, 149.59, 143.36, 136.80, 132.29, 126.77, 122.18, 113.95, 113.71, 55.20, 55.13.

Synthesis of Compound 2

The compound 1 (191.5 mg, 0.44 mmol) and 1,12-dibromododecane (145.0 mg, 0.44 mmol) were weighed and dissolved in 3 mL of acetonitrile solution, and fully stirred at room temperature. The reaction system was fully refluxed for 8 hours at 90° C. After the reaction was completed by monitoring with TLC plates, the solvents were removed by distilling under vacuum. The compound 2 was purified by the silica gel column chromatography in a yield of 34.7%. Results of nuclear magnetic resonance analysis were as follows: $^1$H NMR (500 MHz, DMSO-d6) δ 8.88 (d, 2H), 7.74 (d, 2H), 7.49 (dd, 7H), 7.20 (d, 2H), 6.90 (d, 4H), 4.45 (t, 2H), 3.73 (d, 6H), 3.51 (t, 2H), 1.79 (dd, 4H), 1.23 (s, 16H). $^{13}$C NMR (125 MHz, DMSO-d6) δ 159.99, 159.14, 132.75, 130.42, 130.10, 128.97, 128.24, 126.12, 123.70, 121.22, 114.57, 114.37, 60.38, 55.57, 35.67, 32.68, 30.77, 29.31, 29.28, 29.18, 28.78, 28.55, 27.95, 25.82.

Synthesis of Compound 3

The compound 2 (155.0 mg, 0.20 mmol) was weighed and dissolved in 4-5 mL of pyridine solution, and fully stirred at room temperature. The reaction system was fully refluxed for 8 hours at 90° C. After the reaction was completed by monitoring with TLC plates, the solvents were removed by distilling under vacuum. The target compound 3 was produced by the silica gel column chromatography in a yield of 68.2%. Results of nuclear magnetic resonance analysis were as follows: $^1$H NMR (500 MHz, CD$_3$OD) δ 9.11-8.98 (m, 2H), 8.85-8.66 (m, 2H), 8.60 (t, 1H), 8.12 (s, 2H), 7.86 (d, 2H), 7.50 (d, 5H), 7.38 (s, 2H), 7.13 (d, 2H), 6.84 (s, 4H), 4.66 (s, 2H), 4.50 (s, 2H), 3.89-3.62 (m, 6H), 1.99 (d, 4H), 1.56-1.04 (m, 16H). $^{13}$C NMR (125 MHz, CD$_3$OD) δ 160.33, 159.48, 145.45, 144.54, 144.41, 143.81, 143.77, 141.37, 139.62, 139.58, 136.00, 132.17, 132.14, 129.91, 129.88, 128.32, 128.10, 123.66, 120.69, 113.79, 113.76, 113.41, 113.39, 61.72, 60.69, 54.38, 54.33, 31.10, 30.84, 30.81, 29.76, 29.72, 29.36, 29.33, 29.13, 29.05, 28.68, 25.77.

Example 2

Preparation of the Water-Soluble Organic Fluorescent Molecular Probe

40 μL of compound 3 (1 mM) in a phosphate buffer solution was taken by using a pipette and placed in an ep-tube. 1960 μL of a phosphate buffer solution (pH=7.4) was added into the ep-tube under an ultrasonic condition so that the final concentration of compound 3 was 20 μM. The mixture was stirred for 30 min under room temperature to generate opalescence. In order to verify nano-aggregation behavior thereof, an average particle size thereof measured by a dynamic light scattering experiment was 600 nm, as shown in FIG. 1.

Example 3

Testing Recognition of Lysophosphatidic Acid by the Prepared Fluorescent Molecular Probe and Nanoparticles Through a Scanning Electron Microscope (SEM)

Figure 2:
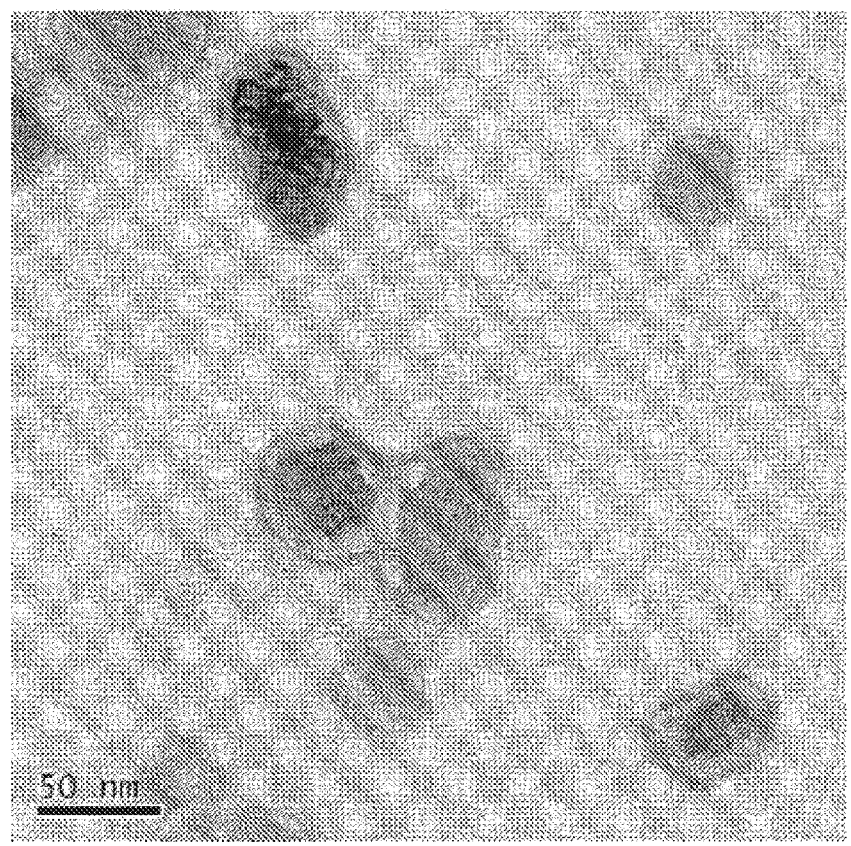
FIG. 2 is a scanning electron micrograph showing recognition of lysophosphatidic acid by the fluorescent molecular probe and nanoparticles according to the disclosure.

40 μL of compound 3 (1 mM) in a phosphate buffer solution was taken by using a pipette and placed in an ep-tube. 1900 μL of a phosphate buffer solution (pH=7.4) was added under an ultrasonic condition, and 60 μL of lysophosphatidic acid (1 mM) in a phosphate buffer solution was added so that the final concentration of the compound 3 in the solution was 20 μM, and the final concentration of lysophosphatidic acid was 30 μM. The mixture was stirred for 30 min at room temperature. A drop of the prepared solution was sucked, and dropped onto a copper grid. Water was absorbed by filter paper. Then the copper grid was air-dried and placed in a transmission electron microscope for observation. A transmission electron micrograph is shown in FIG. 2.

Example 4

Figure 3:
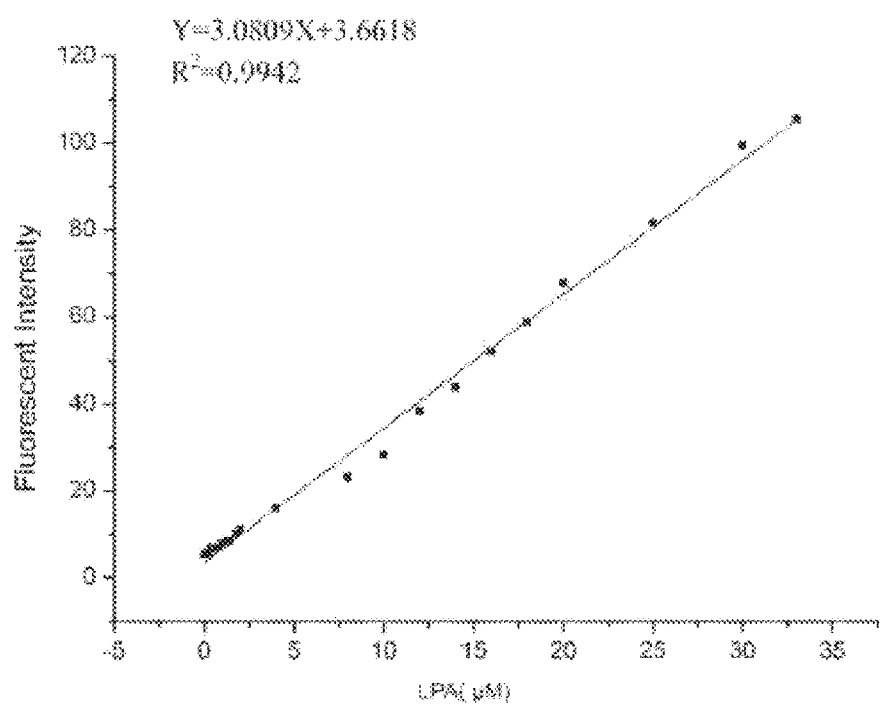
FIG. 3 shows the linear relationship between the fluorescence intensity of the fluorescent molecular probe and nanoparticles according to the disclosure and the concentration of lysophosphatidic acid. An abscissa represents the concentration of lysophosphatidic acid, and an ordinate represents the fluorescence intensity.

A Linear Relationship Between the Fluorescence Intensity of the Fluorescent Molecular Probe and Nanoparticles and the Concentration of Lysophosphatidic Acid A series of different volumes of the stock solution of lysophosphatidic acid in the phosphate buffer solution were respectively added to the system prepared in Example 2, so that the final concentrations of lysophosphatidic acid respectively were 0 μM, 0.2 μM, 0.4 μM, 0.8 μM, 1.0 μM, 1.2 μM, 1.4 μM, 1.8 μM, 2.0 μM, 4.0 μM, 8.0 μM, 10.0 μM, 12.0 μM, 14.0 μM, 16.0 μM, 18.0 μM, 20.0 μM, 25.0 μM, 30.0 μM, 33.0 μM. After all of testing solution were prepared, the testing solutions were mixed uniformly with a vortex. After being incubated for 1 min at room temperature, the fluorescence emission intensity thereof at 557 was measured. As shown in FIG. 3, the results show there is a good linear relationship between the fluorescence intensity of the system at 557 nm and the concentration of lysophosphatidic acid in the range of 0-33 μM.

Example 5

Figure 4:
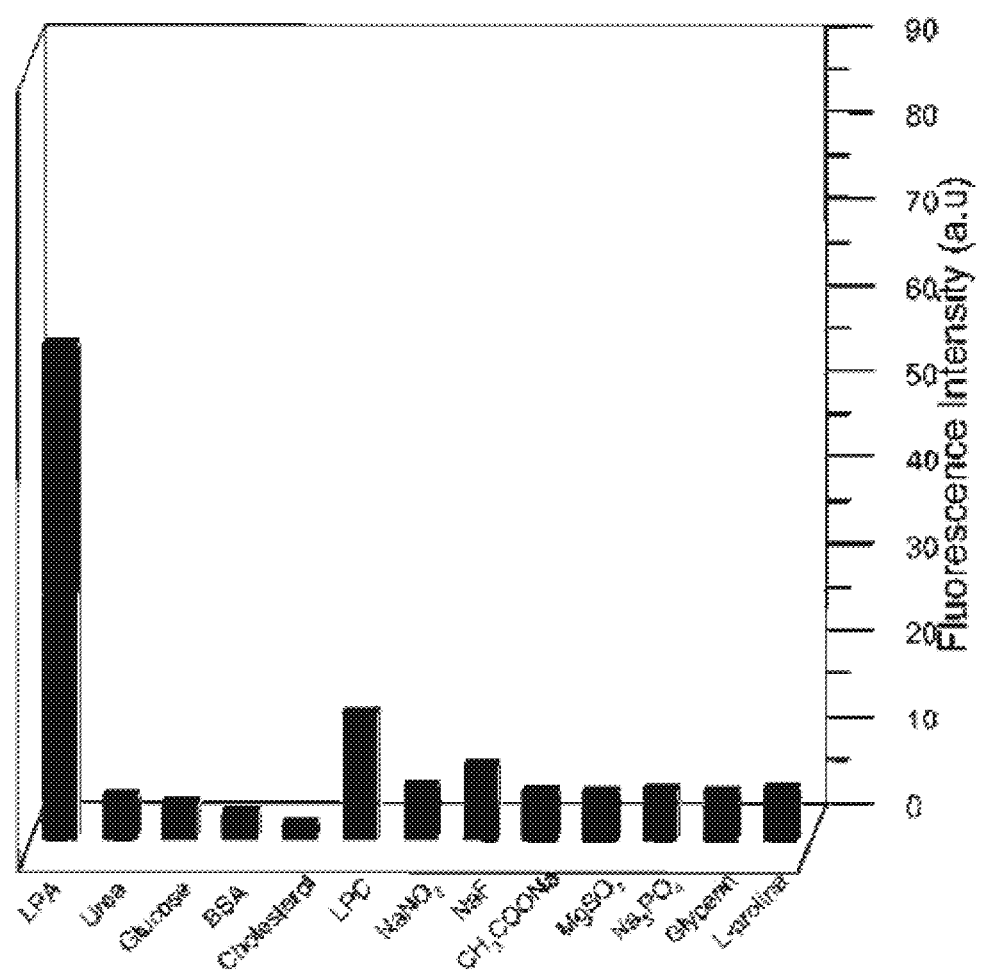
FIG. 4 shows the selectivity of the fluorescent molecular probe and nanoparticles according to the disclosure to lysophosphatidic acid.
Figure 5:
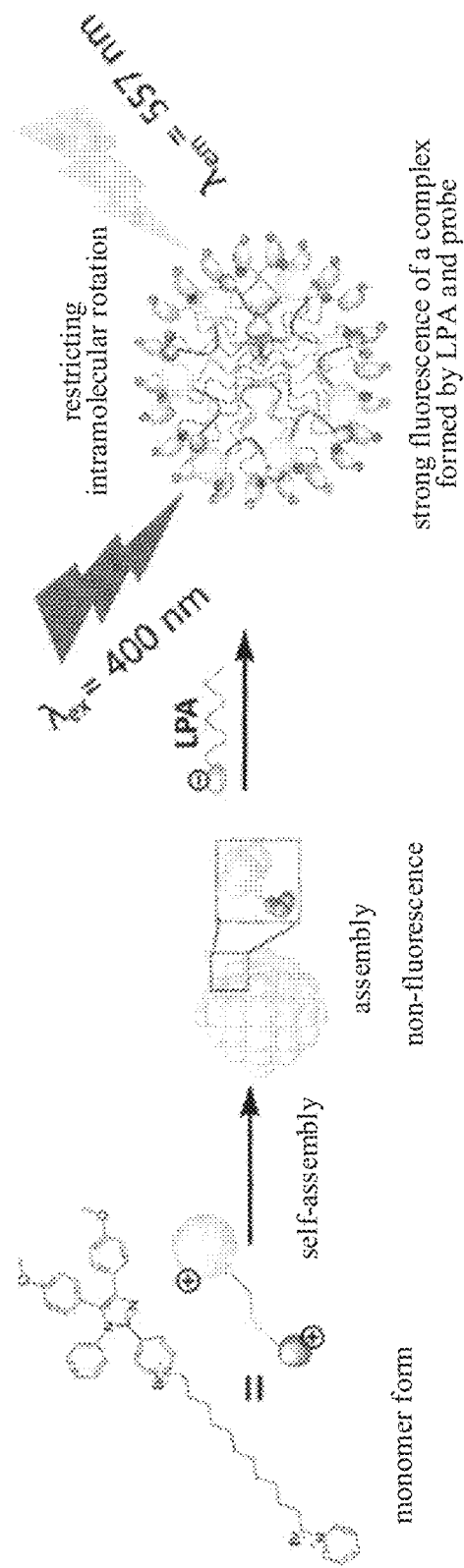
FIG. 5 is a schematic diagram showing the mechanism for detecting lysophosphatidic acid by the fluorescent molecular probe and nanoparticles.

Selectivity of the Organic Fluorescent Nanoprobe to Detection of Lysophosphatidic Acid The prepared fluorescent molecular probe solution was used for evaluating the selectivity of the probe to lysophosphatidic acid. An excitation wavelength of the nanoprobe was 400 nm. The concentration of the compound 3 in the system was 10 μM. Lysophosphatidic acid with a final concentration of 50 μM and L-proline, glycerin, sodium phosphate, magnesium sulfate, sodium acetate, sodium nitrate, sodium fluoride, glucose, urea, and lysophosphatidyl choline (LPC) with a final concentration of 1 mM were respectively added into the system. After fully mixing, the systems were incubated for 1 min at room temperature. Then fluorescence emission spectra thereof were measured and the fluorescence emission intensities at 557 nm were recorded. As shown in FIG. 4, only the system with the addition of lysophosphatidic acid generated strong yellow fluorescence, and the other solutions with the addition of other substances could not be observed to generate yellow fluorescence. The above results show that the organic fluorescent molecular probe and nanoparticles have good selectivity and practical applicability for detecting lysophosphatidic acid.

The invention claimed is:

1. A fluorescent molecular probe, wherein the fluorescent molecular probe has a structure of Formula 1:

wherein the fluorescent molecular probe is water-soluble and has an aggregation-induced emission effect, and the fluorescent molecular probe is used for specifically recognizing lysophosphatidic acid.

2. The fluorescent molecular probe of claim 1, wherein the fluorescent molecular probe is formed by linking a tetrasubstituted imidazole ring, a dodecyl chain and a pyridine ring with formation of a salt.

3. A fluorescent nanoprobe, wherein the fluorescent nanoprobe is formed by self-assembly of the fluorescent molecular probe of claim 1, and the fluorescent nanoprobe is used for specifically recognizing the lysophosphatidic acid.

4. A method for preparing the fluorescent molecular probe of claim 1, wherein the method comprises the following steps:

1) 4-formylpyridine, aniline and anisil undergoing a one-pot cyclization reaction in an acetic acid/ammonium acetate system, to obtain an intermediate of Formula 2;

2) the intermediate of Formula 2 and 1,12-dibromododecane undergoing a nucleophilic substitution reaction, to obtain an intermediate of Formula 3; and 3) the intermediate of Formula 3 and pyridine undergoing a nucleophilic substitution reaction, to obtain a target product, Formula 1

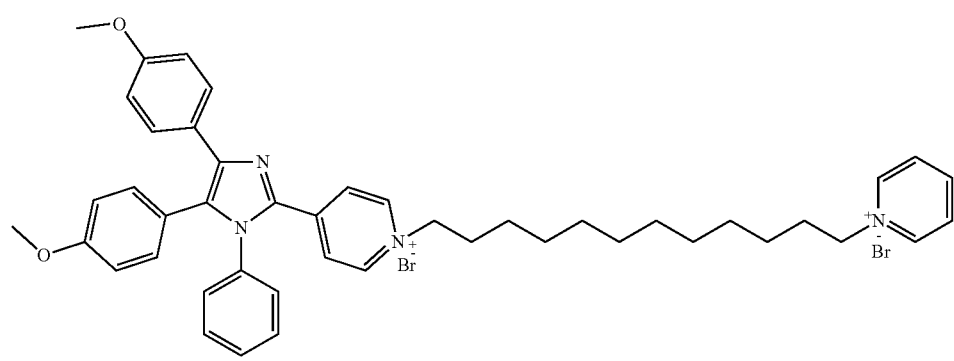

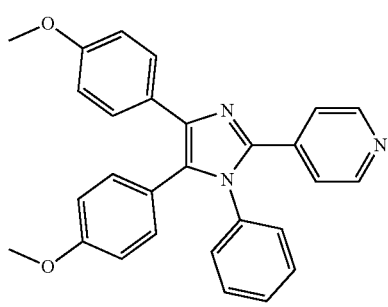

Formula 2

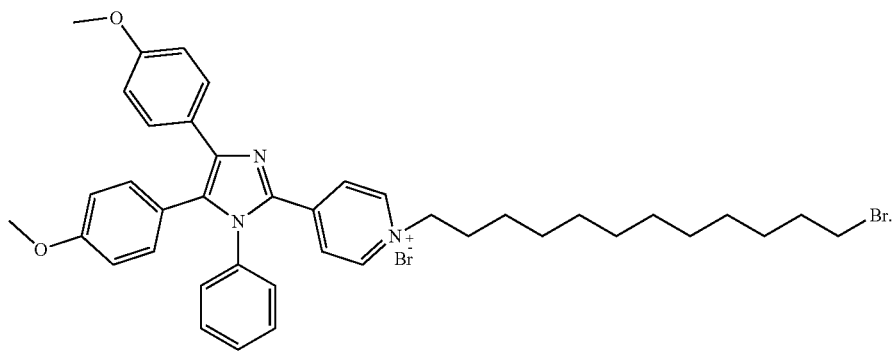

Formula 3

5. The method of claim 4, wherein:
a reaction process in the step 1) is as follows: dissolving the 4-formylpyridine and the aniline in a glacial acetic acid solvent and stirring for 0.5-1.5 hours at room temperature, and then adding the anisil and ammonium acetate, reacting for 6-12 hours at 120° C.;
reaction conditions in the step 2) are as follows: using acetonitrile as a solvent, and reacting for 6-10 hours at 90° C.; and
reaction conditions in the step 3) are as follows: using the pyridine as a solvent, reacting for 6-10 hours at 90° C.

6. A method for preparing the fluorescent nanoprobe of claim 3, comprising: dissolving the fluorescent molecular probe into an organic solvent, to yield an obtained mixture, adding the obtained mixture into an aqueous solution, performing ultrasonic treatment, and obtaining the fluorescent nanoprobe.

7. The method of claim 6, wherein the organic solvent is selected from at least one of methanol, ethanol, dimethylformamide, tetrahydrofuran, dimethyl sulfoxide, acetone, or acetonitrile, and the aqueous solution is selected from pure water, physiological saline, a phosphate buffer solution (PBS), a tris(hydroxymethyl)aminomethane hydrochloride buffer solution or a 4-hydroxyethylpiperazine ethanesulfonic acid buffer solution.

* * * * *